(12) United States Patent
Olroyd

(10) Patent No.: US 7,625,373 B2
(45) Date of Patent: Dec. 1, 2009

(54) CABLE ANCHOR FOR ATTACHING ELASTIC CABLE TO A BONY SUBSTRATE

(75) Inventor: Craig D. Olroyd, Santa Barbara, CA (US)

(73) Assignee: Poly 5 Group, LLC, Santa Barbara, CA (US)

( * ) Notice: Subject to any disclaimer, the term of this patent is extended or adjusted under 35 U.S.C. 154(b) by 590 days.

(21) Appl. No.: 11/478,763

(22) Filed: Jun. 30, 2006

(65) Prior Publication Data
US 2008/0004624 A1    Jan. 3, 2008

(51) Int. Cl.
*A61B 17/82* (2006.01)
(52) U.S. Cl. .................................................... 606/74
(58) Field of Classification Search .................. 606/74, 606/263, 278, 103, 232, 113; 24/11 R, 115 H, 24/127
See application file for complete search history.

(56) References Cited

U.S. PATENT DOCUMENTS

| | | | | |
|---|---|---|---|---|
| 3,597,808 | A * | 8/1971 | Johnson | 24/127 |
| 4,988,351 | A * | 1/1991 | Paulos et al. | 606/232 |
| 5,108,397 | A * | 4/1992 | White | 606/60 |
| 5,665,088 | A * | 9/1997 | Gil et al. | 606/74 |
| 6,093,190 | A * | 7/2000 | Mattchen | 606/74 |
| 6,391,030 | B1 * | 5/2002 | Wagner et al. | 606/74 |

* cited by examiner

*Primary Examiner*—Pedro Philogene
(74) *Attorney, Agent, or Firm*—Laura N Tunnell

(57) ABSTRACT

An anchoring fastener is adapted for attaching an elastic cable to a substrate, and is suitable for use in stabilizing and fixating a bony fracture with an elastic cable having known diameter and elastic properties. The invention includes: a generally annular collar, a deformable centering ring seatable inside the annular collar, and an anchor post adapted to be passed through the annular collar and ring. A loop or bight of cable passed around a shoulder of the anchor post is retained under compression in a defined annular void defined between a shoulder of the post and a cylindrical bore in the annular collar.

20 Claims, 3 Drawing Sheets

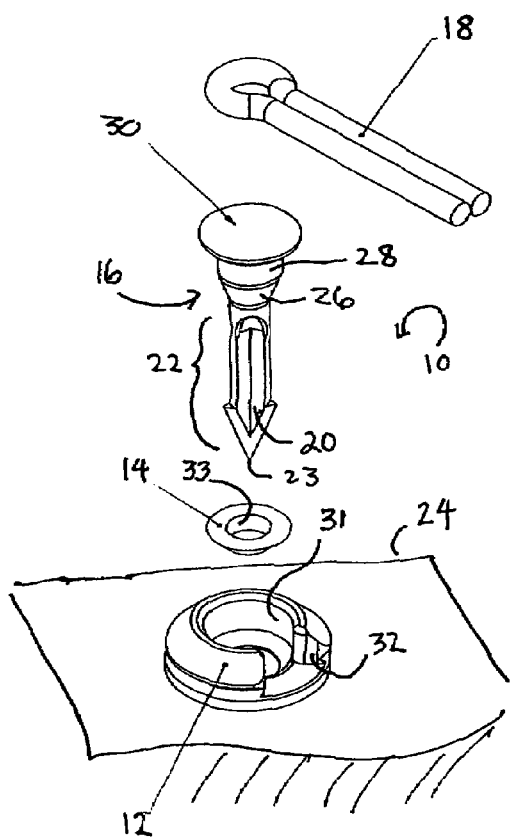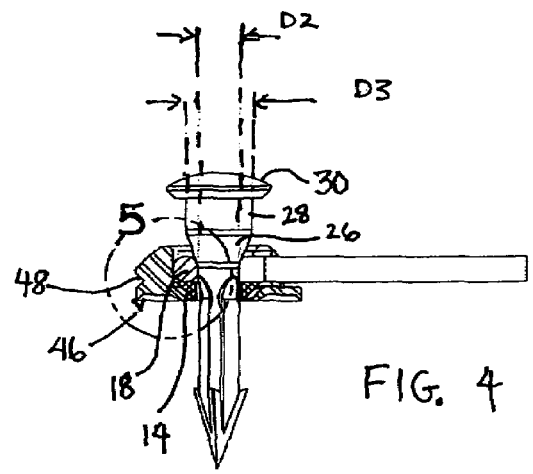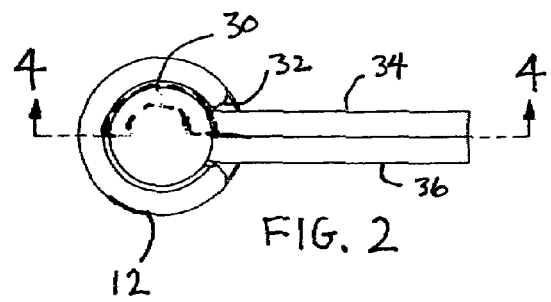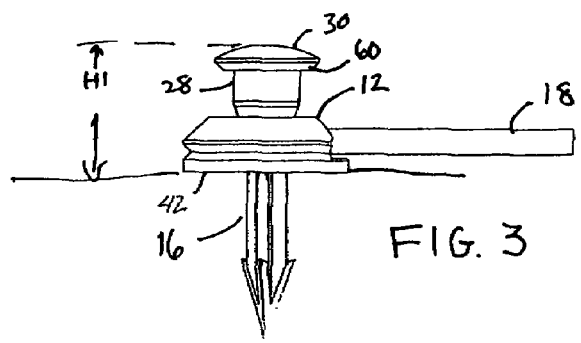

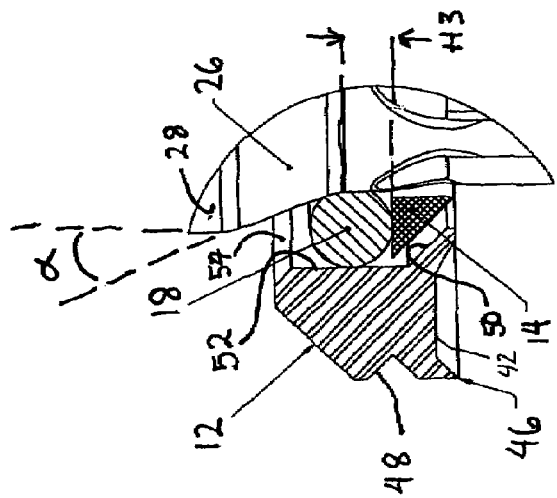
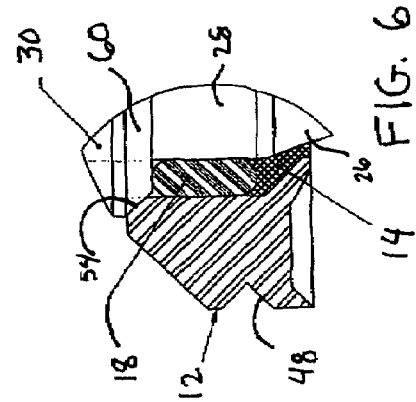
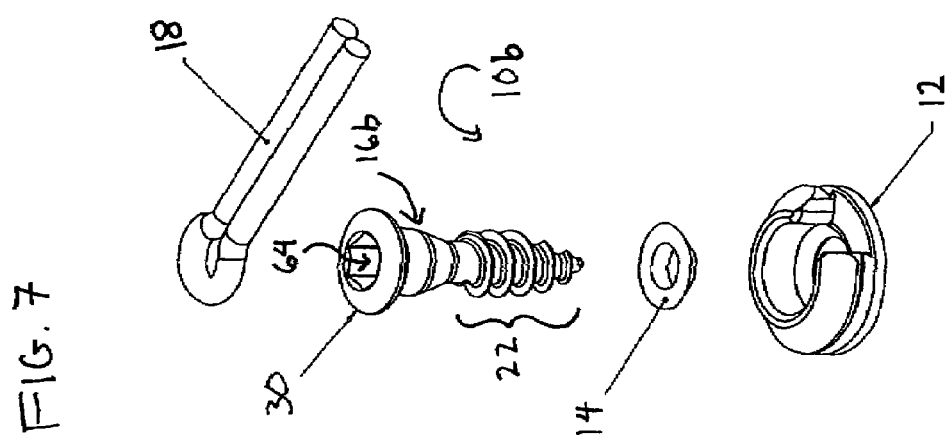

CABLE ANCHOR FOR ATTACHING ELASTIC CABLE TO A BONY SUBSTRATE

BACKGROUND OF THE INVENTION

1. Field of the Invention

This invention relates to tools and methods for orthopedic surgery generally and more specifically to bone screws and cables for fixation of fractured bones.

2. Description of the Related Art

In various medical procedures wires or cables are used to join fractured bones. Typically, metal alloy cables are preferred; but synthetic polymer cables are sometimes employed. For example, U.S. Pat. No. 6,093,190 to Mattchen describes a method of using elastomeric cables to stabilize and compress fractured bones, by spanning a network of tensioned cables across a fracture. Such a network can provide stable fixation of a fracture in both linear and torsional directions. The method disclosed also provides a tensile preload across the fracture, tending to compress the fracture and maintain fixation despite tensile and shear loads (such as those resulting from movement, weight bearing and bone remodeling).

Many polymeric, elastic cable constructions have desirable engineering properties and are known to be biocompatible. However, manipulation and fixation of some polymer cables is inconvenient with traditional methods and fasteners. Metal wires and cables are easily joined at their ends using surgical knots or known surgical fasteners, including screws. Various known cable tensioner devices may be employed to attain desired tensioning in loops formed by tied or crimped wires and cables. On the other hand, certain elastic, polymer cables are not so easily fixed. Cables engineered for extreme elongation under tension tend to change diameter in response to tension, and tend to escape from conventional gripping devices. The problem is further exacerbated by the incidental fact that many polymer cables (or coatings) have a low coefficient of friction, and are thus prone to slip. Gripping such a cable with extremely localized, high pressure is not an adequate solution, because localized high compression can lead to failure by cutting the cable.

An improved method and device is desirable for securely anchoring high strength, polymeric cables to a bony structure.

SUMMARY OF THE INVENTION

In view of the above problems, the present invention provides an anchoring fastener for attaching an elastic cable to a substrate, suitable for use in stabilizing and fixating a bony fracture with an elastic cable having known diameter and elastic properties. The invention includes: a generally annular collar having a top, a bottom, and a first bore, the first bore having an upper, cylindrical portion above an inwardly tapering lower throat; a deformable ring capable of seating inside the annular collar, said deformable ring having a second bore and a generally conical outside bevel, the generally conical outside bevel before deformation coaxially seating in the lower throat of said annular collar; and an anchor post having an expanded head at an upper end, a cylindrical shoulder below said head, a lower, penetrating shaft, and a tapering transition between said cylindrical shoulder and the penetrating shaft. The penetrating shaft is adapted to be passed through said second bore in said deformable ring and penetrate into a substrate under thrusting force.

The transition is dimensioned to compress the deformable ring between said lower throat of said collar and said tapering transition, when said anchor post is thrust downward to seat in said collar. When the anchor post is seated with the head in abutting relationship with the top of said collar, an annular void of predetermined volume is defined between the shoulder of the post and the first bore. The annular void thus defined has dimensions predetermined to compressively secure the elastic cable having known diameter and elastic properties.

In one embodiment, the anchor post is a penetrating (preferably fluted) nail. In another embodiment, the anchor post has tapping screw threads to assist penetration into the substrate.

These and other features and advantages of the invention will be apparent to those skilled in the art from the following detailed description of preferred embodiments, taken together with the accompanying drawings, in which:

BRIEF DESCRIPTION OF THE DRAWINGS

FIG. 1 is an exploded perspective view of an anchor device in accordance with the invention, in relation to a loop of cable;

FIG. 2 is a top view of the device of FIG. 1;

FIG. 3 is an elevation view of the anchor device, in a partially assembled configuration;

FIG. 4 is a sectional view taken along the section line 4 in FIG. 3, with the device in the partially assembled configuration;

FIG. 5 is a magnified detail view of a portion of the sectional view in FIG. 4;

FIG. 6 is a magnified detail view of the same section as presented in FIG. 5, except that the device is shown here in its fully assembled configuration;

FIG. 7 is an exploded perspective view of a second embodiment of the invention, in which the anchor post has a threaded penetration lower portion.

DETAILED DESCRIPTION OF THE INVENTION

Figure 8:
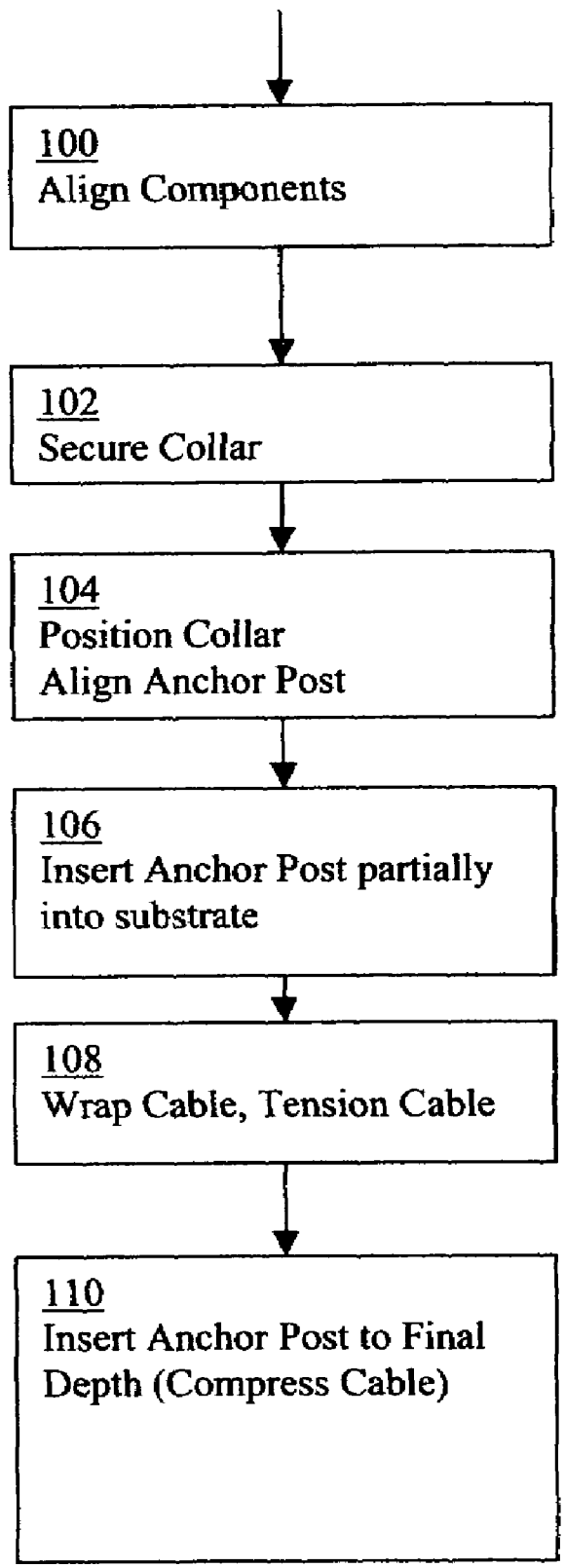
FIG. 8 is a flow chart of a method in accordance with the invention for fixing an elastic cable to a substrate.

As shown in FIG. 1, an anchor (generally designated 10) a device in accordance with the invention has at least 3 general components: a compression collar 12, a centering ring 14, and an insertable anchor post 16. A cable 18 is also shown as part of a system of cable and anchor in accordance with a system of the invention. The invention is intended to anchor a high strength, elastic cable capable of considerable elongation; it is assumed that the diameter and elastic properties of the cable are known in advance, allowing the dimensions of the anchor components to be predetermined based on the cable dimensions and properties.

The element 16 is generically described as an insertable anchor post. In one embodiment (as shown in FIG. 1) a penetrating nail provides a suitable insertable anchor post 16. In another embodiment, (discussed below) a screw serves as an insertable anchor post 16. Various designs of nails, screws, brads, tacks, or other penetrating post-like anchors may be employed, provided they are designed to interact with the compression collar, centering ring, and cable 18 in a manner substantially as described below, and further provided that the post 16 is capable of forcible insertion into a hard substrate (such as bone).

In both nail and screw embodiments, the anchor post 16 is suitably fabricated from a high strength, substantially rigid, bio-compatible material such as a titanium alloy or a stainless steel alloy. In the nail embodiment (shown in FIG. 1) flutes 20 are preferably provided in the lower, penetrating portion 22 of the post, which terminates in a sharp, cutting tip 23. Such bevels enhance cutting during penetration into a hard substrate 24 (such as a bone). Above the penetrating portion 22 of the anchor post, a generally tapering conical transition 26 expands to a larger diameter, generally cylindrical shank or shoulder 28. The shank is capped by an even larger diameter head 30.

The compression collar 12 is generally annular in form, having a central bore 31. The generally annular form of the collar is interrupted by a sidewards oriented port 32, which allows entry and exit of cable 18.

The centering ring 14 generally resembles a conical washer having a central, axial bore 33 sized to accept the lower portions of the anchor post 16. The centering ring should preferably be of a deformable, biocompatible material (for example, an acetal polymer). During assembly the centering ring is required to deform in response to compressive forces, as described below.

During assembly of the anchor device, the anchor post 16 passes through the central, axial bore 33 in the centering ring 14, then through the bore 31 in compression collar 12. The head 30 is arranged to receive thrust from a thrusting tool such as a screw or impact device (not shown), generally in the same manner as driving home a rivet. In response to thrust applied to the head, The lower, forward cutting tip 23 penetrates into the substrate (bone) 24, skewering the centering ring and seating the ring in the compression collar. Before the insertion is complete, a loop of cable 18 can be passed over the head 30 and tensioned around the shoulder 28 of the anchor post (by a method described in more detail below). Unlike conventional rivets, the apparatus of the invention is specifically adapted to engage and retain the elastic cable 18 by fastening a loop or bight of cable to the anchor post 16. When used as described below ("method of use") the anchor of the invention securely engages a loop of cable 18, retaining the cable and (in some applications) relieving a free or "working" end of the cable for further placement, while isolating the tension on the loaded end of the same loop.

The top view in FIG. 2 shows the anchor of the invention as it would appear in either a fully or partially seated configuration, arranged to secure a loop of cable having emergent ends 34 and 36 (shown for convenience in a parallel and contiguous configuration). Either end 34 or 36 may be loaded, or both; the anchor 10 isolates the load in 34 from that in 36.

Explanation of the invention is facilitated by considering two distinct, static configurations of the components: we consider the apparatus first in a static, partially driven configuration, proceeding to consider the static, fully seated position after the anchor post 16 is inserted to final depth.

Accordingly, FIG. 3 shows in elevation (side) view a partially driven position of the apparatus, in relation to a cable 18. The lower, penetrating portion 22 of anchor post 16 has been driven partially into a bony substrate 24, but has not been sunk to its final, fully seated depth. Because the sinking is incomplete, the cylindrical shoulder 28 of the post protrudes above the top of the collar 12.

The sectional view in FIG. 4 (a portion of which is magnified in FIG. 5) reveals further details of the collar 12, compression ring 14 in relation to cable 18 and anchor post. FIG. 4 shows the apparatus in its partially driven position.

The generally annular compression collar 12 has a top countersink bevel 54 (adapted to abut and be retained by screw head 30) a bottom surface 42 (adapted to seat on and engage the substrate) and a central bore 31. The bottom surface 42 of Compression collar 12 preferably has a textured or sharpened feature or features 46 which securely engage the substrate 24. Preferably, an outer groove, slot, or other feature 48 runs circumferentially around the outside rim of compression collar 12. This feature is extremely advantageous in that it facilitates engagement with a fixation tool, and allows relief of bending forces that would otherwise stress the anchor post during installation.

The bore 31 of the generally annular compression collar has three distinct portions: A lower, generally conically tapered, funnel-like throat 50; a middle, generally cylindrical bore 52; and an upper countersunk bevel 54 adapted to seat the head 30 of the anchor post 16. The conically tapered throat 50 receives and seats the similarly conical centering ring 14 which coaxially surrounds the anchor post 16. The seating of the taper centering ring in the tapered throat 50 greatly facilitates proper centering. Above the tapered throat 50 the middle bore 52 coaxially surrounds the conical transition 26 of the nail, clamping a section of cable 18 between the inner wall of middle bore 52 and the tapering transition 26 of the nail. The dimensions of the transition 26, the throat 50, the middle bore 52, and the compression ring 14 are all pre-determined to produce a pre-designed elastic interference with a cable 18 having known diameter and elastic properties (when the post 16 is driven to the partial assembly position as shown in FIG. 5). Therefore, further insertion of the anchor post is somewhat resisted in the partially inserted position.

Driving the anchor post 16 further moves the assembly to the final position as illustrated in FIG. 6. This figure shows the same (magnified) cross section as FIG. 5, except that the components are shown in an assembled position, with the anchor post 16 fully inserted and the cable 18 secured by compression. As the anchor post 16 is inserted (driven) into the substrate, the centering ring is forced to deform (specifically, by contracting in the radial dimension and expanding in the axial direction). In other words, driving the nail forcibly downward in the figure forces the cable 18 and the centering ring to expand along a taper defined by the transition 26 (preferably at an angle $\alpha$ of substantially 20 degrees) from diameter D2 to Diameter D3. The inside bore 52 of the compression collar 12 constrains this expansion and forces the cable to compress into an defined annular void of generally rectangular cross-section and predetermined volume. The deformable property of the centering ring allows it to reshape into the diminished space between the nail and the lower throat of the compression collar. Similarly, as the anchor post 16 is forcibly driven into the substrate the cable 18 deforms by contraction in the radial direction (while expanding in the axial direction) in response to the contracted radial clearance between nail shank and the collar bore. The radial compression of the cable tends to grip the cable between the cylindrical shoulder 28 and and the cylindrical collar bore 52. This gripping tendency, together with the friction between the cable and the shoulder around which it is wrapped, secures the cable in reaction to tensile loading along the cable axis. The cable is thus retained by both clamping forces and the friction of the wrap around a post, in the manner of a hitch knot or friction belay. The centering ring 14 acts as a variable annulus during insertion of the anchor post 16, constantly reacting the downward force on the cable and preventing the cable from being unduly pinched between the anchor post 16 and the bottom throat of the compression collar 12.

All rigid surfaces that contact the cable should preferably be surfaces textured to 16 RMS (root-mean-squared micro inches) or less. This prevents fraying of the cable during installation and results in higher fatigue strength under cyclic loading.

Once the nail is driven into the fully seated position (shown in FIG. 6), an outside bevel 60 on the nail head 30 seats in the complementary countersink bevel 54 on compression collar 12, preventing further insertion and securing the collar, cable, and centering ring in position.

Multiples of the anchor 10 can be secured in series along a single cable, for example in a zig-zag or weaving pattern with a desired tension in each or all spans of cable, tending to draw the anchor points together in a desired pattern of tension vectors. As such, these anchor assemblies are advantageous for use in fixing bony fractures, for example in the procedure described in U.S. Pat. No. 6,093,190 (Mattchen).

FIG. 7 shows a variation or second embodiment of the invention. As will be apparent, this embodiment is substantially similar to that shown in FIG. 1, but differs in that the lower portion 22 of screw-anchor post 16b is threaded with a bone-tapping thread (rather than the fluted nail shown at in FIG. 1). In addition, the head 30 of this "bone-screw embodiment" should have an easily engaged feature for applying torque to the screw (such as a hex head or hexagonal socket). Any of various known head patterns could be employed, in connection with complementary driver configurations.

The bone-screw embodiment as shown in FIG. 7 is advantageous for penetrating certain types of substrates, including harder bony tissues. Assembly of the variant embodiment is substantially the same as described above; except that the screw-anchor post 16b must be rotated during insertion (both to the partially assembled and final insertion positions). Note that in the final, fully seated configuration the compression of the cable 18 and the compression ring 14 both rotationally couple the collar to the screw-anchor post 16b. Thus, any torque imparted by the tensioned cable is transferred via the collar 12 to the gripping feature 46 and in turn to the bony substrate 24. The torque is largely isolated from the screw-anchor post 16b, and does not tend to loosen or tighten the screw after assembly.

The cooperation of the various features of the apparatus as shown and described become more apparent in the context of the method of attaching the apparatus to a substrate and cable, as described below.

Method of Use:

A method of attaching and assembling the apparatus to fix a cable to a substrate invention shown in the flow diagram of FIG. 8.

Initially, in step 100, the multiple components (anchor post 16, collar 12, and centering ring 14) are aligned for insertion at a desired location on a substrate, typically a bony surface. The anchor post 16 is inserted into the central bore of the centering ring 14, and both are aligned to insert coaxially through the compression collar 12 (as shown in exploded FIG. 1). The collar is then secured (step 102) by a tool, for example a specific driving tool including a collet or other gripping device feature adapted to grip the collar. Gripping and axial alignment of the collar are facilitated greatly by the circumferential, annular groove or slot 48 provided on the outside of the collar; a collet or other tool can easily be adapted to engage the collar via the groove.

The collar is then maneuvered into contact with the substrate in the desired position (step 104). The sharp edge or feature 46 on the collar should embed into the substrate slightly, thus helping to maintain the desired location during the installation process. The coaxial alignment of the anchor post 16 with the collar 12 is maintained by the centering ring 14, said centering ring having an outer diameter that closely fits inside the major counter bore or tapered throat of the collar.

Once aligned, the anchor post 16 is driven into the substrate to the height shown in FIG. 5 (incomplete insertion, step 106). This height locates the small diameter (D2) of the anchor post a distance of H3 above the centering ring providing minimally sufficient space for the uncompressed cable, as shown.

Next, (step 106) with the anchor post 16 rigidly located (partially driven) within the substrate, a loop of cable 18 is wrapped around the diameter D2 of the anchor post 16 and seated onto the top surface of the centering ring 14 as shown in FIG. 5. The free end (head 30) of the anchor post 16 should preferably be held concentric to the collar by a driving tool, for example by a tool having a bore adapted to tightly receive the head or upper portion of the anchor post 16. The upper portion of the anchor post 16 should preferably be strongly supported by the driver as against bending or shearing forces, such as would be applied when the cable loop is under significant tension.

Supporting the anchor post 16 at both ends (at top by tool, at bottom by the substrate) allows the cable to be tensioned easily to a desired load, without significant bending of the post or damage to the substrate; reactive forces are provided by the tool and/or the lower face of the collar in contact with the substrate. More specifically, manual force is applied to an elongated, rigid tool which receives the head of the anchor post 16; the rigid tool also holds the axis of the head coaxial with the axis of the collar, being secured by collet to the groove 48 in the collar 12. During tensioning, the contact between the lower face or flange of the collar 12 and the substrate provides a fulcrum for the manual application of moment to counteract the cable tension, relieving the anchor post from strong bending moment. The cable loop can thus be tensioned on at least one loaded end (while supporting the head to counteract the tension).

With all of the components located in the incomplete insertion position (FIG. 5), the anchor post 16 is then driven (step 110) deeper into the substrate to a final depth (FIG. 6). This could be performed by forcibly, axially driving a coaxial rod or pin downwards against the head 30 of the anchor post 16, forcing insertion of the post into the substrate until the head 30 abuts the top of collar 12 (seating in the countersink optionally provided). As the post is inserted into the substrate, the motion of the anchor post 16 forces the cable and the centering ring to expand along the transition 26 (suitably 20 degrees) from the diameter D2 to the diameter D3, as described above. The cable is in this configuration confined to the annular void defined between the shoulder 28 of the anchor post (on the inside) and inside wall of the bore 52 in the compression collar 12. Some deformation of the cable is expected, as shown in FIGS. 5 and 6.

Only slight variation of the method is required to adapt to the embodiment of the apparatus as shown in FIG. 7 (bone screw insertion). In step 110, rather than merely driving the anchor forcibly axially downward, a screwdriver can be engaged with the head 30 and the screw 16b driven to final depth by a combination of rotation and axial thrust. The screwdriver may be integrated with a combination collet and cable winding tool, or might be inserted through a bore in said tool.

The process may then be repeated as needed at different points along the cable, fixing to various points on a substrate as desired. Various mesh, zigzag, and matrix patterns may be employed in a manner similar to suturing. The method and apparatus of the present invention may suitably be use in connection with the methods described in U.S. Pat. No. 6,093, 190, but are not limited to that context.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

I claim:

1. An anchoring fastener for attaching an elastic cable to a substrate, suitable for use in stabilizing and fixating a bony fracture with an elastic cable having known diameter and elastic properties, comprising:
   a generally annular collar having a top, a bottom, and a first bore, said first bore having an upper, cylindrical portion above an inwardly tapering lower throat;
   a deformable ring capable of seating inside said annular collar; and
   an anchor post having an expanded head at an upper end, a cylindrical shoulder below said head, a lower, penetrating shaft, and a tapering transition between said cylindrical shoulder and said penetrating shaft;
   wherein said penetrating shaft is adapted to be passed through a second bore in said deformable ring and to penetrate into the substrate;
   and wherein said transition is dimensioned to compress said deformable ring seated in said collar when said anchor post is forcibly urged downward through said collar to penetrate into the substrate;
   and wherein, when said anchor post is seated with said head in abutting relationship with said top of said collar, an annular void of predetermined volume is defined between said shoulder of said post and said bore, said annular void having dimensions predetermined to compressively secure the elastic cable having known diameter and elastic properties.

2. The anchoring fastener of claim 1, wherein said generally annular collar has a sidewise directed port to accept entry and exit strands of said cable, said strands defining a bight of a cable passing around said post and included within said annular void.

3. The anchoring fastener of claim 2, wherein said penetrating lower portion of said anchor post comprises a threaded screw.

4. The anchoring fastener of claim 3, wherein a lower face of said collar has a sharp feature to engage the substrate.

5. The anchoring fastener of claim 3, wherein an outside rim of said collar has a generally circumferential groove, suitable for engaging with a gripping tool.

6. The anchoring fastener of claim 3, wherein said transition tapers at an angle of 20 degrees with respect to a long axis of said anchor post.

7. The anchoring fastener of claim 3, wherein at least a portion of said post and said collar are textured with a maximum surface roughness of 16 RMS microinches.

8. The anchoring fastener of claim 2, wherein said penetrating portion of said anchor post comprises a nail.

9. The anchoring fastener of claim 8, wherein said nail is fluted.

10. The anchoring fastener of claim 8, wherein a lower face of said collar has a sharp feature to engage the substrate.

11. The anchoring fastener of claim 8, wherein an outside rim of said collar has a generally circumferential groove, suitable for engaging with a gripping tool.

12. The anchoring fastener of claim 8, wherein said transition tapers at an angle of 20 degrees with respect to a long axis of said anchor post.

13. The anchoring fastener of claim 8, wherein at least a portion of said post and said collar are textured with a maximum surface roughness of 16 RMS microinches.

14. A system of elastic cable and at least one cable fastener, suitable for use in stabilizing and fixating a bony fracture with an elastic cable, comprising:
   an elastic cable having known diameter and elastic properties; and
   at least one cable fastener, comprising:
   a generally annular collar having a top, a bottom, and a first bore, said first bore having an upper, cylindrical portion above an inwardly tapering lower throat;
   a deformable ring capable of seating inside said annular collar; and
   an anchor post having an expanded head at an upper end, a cylindrical shoulder below said head, a lower, penetrating shaft, and a tapering transition between said cylindrical shoulder and said penetrating shaft;
   wherein said penetrating shaft is adapted to be passed through a second bore in said deformable ring and to penetrate into a substrate under thrusting force;
   and wherein said transition is dimensioned to compress said deformable ring between said lower throat of said collar and said tapering transition, when said anchor post is forcibly urged downward through said collar to penetrate into the substrate;
   and wherein, when said anchor post is seated with said head in abutting relationship with said top of said collar, an annular void of predetermined volume is defined between said shoulder of said post and said bore, said annular void having dimensions predetermined to compressively secure the elastic cable having known diameter and elastic properties.

15. The system of claim 14, wherein said generally annular collar has a sidewise directed port to accept entry and exit strands of the cable, said strands defining a bight of a cable passing around said post and included within said annular void.

16. The system of claim 14, wherein a lower face of said collar has a sharp feature to engage the substrate.

17. The system of claim 14, wherein an outside rim of said collar has a generally circumferential groove, suitable for engaging with a gripping tool.

18. The system of claim 14, wherein said transition tapers at an angle of 20 degrees with respect to a long axis of said anchor post.

19. The system of claim 14, wherein at least a portion of said post and said collar are textured with a maximum surface roughness of 16 RMS microinches.

20. A method of fastening an elastic cable to a substrate, suitable for use in stabilizing and fixating a bony fracture with an elastic cable, comprising the steps:
   placing a generally annular collar on the substrate;
   inserting a penetrating anchor post through an axial bore of said annular collar, through a centering ring seated in said collar, and into the substrate to a first depth;
   passing the elastic cable around said anchor post and inside a bore in said annular collar;
   engaging said annular collar with a supporting tool;
   supporting a head end of said anchor post;
   tensioning said cable passed around said anchor post while supporting said head of said anchor post, said anchor post having a penetrating end supported by said substrate;
   compressing said cable in an annular void between a shoulder of said anchor post and said bore of said annular collar, by driving said penetrating anchor post further to a second, final depth.

* * * * *